United States Patent [19]

Bauer et al.

[11] 4,233,982
[45] Nov. 18, 1980

[54] TROCAR SLEEVES HAVING A BALL VALVE

[75] Inventors: Siegfried Bauer, Heidelsheim; Manfred Boebel, Oetisheim, both of Fed. Rep. of Germany

[73] Assignee: Richard Wolf GmbH, Knittlingen, Fed. Rep. of Germany

[21] Appl. No.: 959,561

[22] Filed: Nov. 13, 1978

[30] Foreign Application Priority Data

Nov. 24, 1977 [DE] Fed. Rep. of Germany ....... 7735963

[51] Int. Cl.³ ...................... A61B 17/34; F16K 51/00
[52] U.S. Cl. .................................. 128/347; 251/149.2
[58] Field of Search ................ 128/349, 347, 350 R, 128/350 V, 4; 251/149.2, 149.3; 27/24 A

[56] References Cited

U.S. PATENT DOCUMENTS

| | | | |
|---|---|---|---|
| 1,497,054 | 7/1924 | Allabach | 251/149.2 |
| 1,818,508 | 9/1931 | Scott | 251/149.2 |
| 1,858,766 | 5/1932 | Dabroski | 251/149.2 |
| 2,641,485 | 6/1953 | Dupuy | 251/149.2 |
| 3,288,142 | 10/1966 | Hakim | 128/350 V |
| 3,730,216 | 4/1973 | Arnett et al. | 251/149.2 |
| 3,754,564 | 9/1973 | Naumburg et al. | 251/149.2 |
| 3,768,102 | 11/1973 | Kwan-Gett et al. | 128/349 R |
| 3,897,810 | 8/1975 | Arnett et al. | 251/149.2 |
| 3,911,977 | 10/1975 | Berger | 251/149.2 |
| 4,007,909 | 2/1977 | Buseth et al. | 251/149.2 |

FOREIGN PATENT DOCUMENTS

| | | | |
|---|---|---|---|
| 201293 | 3/1908 | Fed. Rep. of Germany | 251/149.3 |
| 1267377 | 12/1968 | Fed. Rep. of Germany | 128/4 |
| 2284303 | 1/1976 | France | 128/4 |

*Primary Examiner*—Robert W. Michell
*Assistant Examiner*—C. W. Shedd
*Attorney, Agent, or Firm*—Kinzer, Plyer, Dorn & McEachran

[57] ABSTRACT

A trocar sleeve of the kind having a widened part forming a housing between the distal portion of the sleeve and its proximal portion, which latter extends from a plug for the widened housing part, and a normally closed ball valve in the widened housing part openable by a trocar passing through the sleeve.

The widened part forming the housing receives an insert of U-shaped cross section secured to the plug to stress an inserted sealing gasket of deformation-resistant plastics material which provides a valve seating. The space in the U formed by the insert forms a space for the ball of the ball valve to move in, and the ball, is connected to a shaft insertable in the insert and carrying a tangentially loaded helical spring.

2 Claims, 5 Drawing Figures

TROCAR SLEEVES HAVING A BALL VALVE

BACKGROUND OF THE INVENTION

This invention relates to trocar sleeves (sometimes referred to an cannuli), of the kind having a widened part forming a housing between the distal portion of the sleeve and its proximal portion, which latter extends from a plug for the widened housing part, and a ball valve in the widened housing part which ball valve is normally closed by resilient means and which is openable by a trocar passing through the sleeve. Hereinafter such a trocar sleeve will be referred to as "of the kind described".

It is known to provide trocar sleeves or cannuli between their proximal and distal portions with a widened part which forms a housing and in which a magnetic flap valve is resiliently mounted, as described in German Gebrauchsmuster No. 7,430,345 and British Patent Specification No. 1,482,857, so that the sleeve may be sealed after the trocar has been withdrawn and in this way any escape of gas from say, an abdominal cavity, can be prevented. Practical experience has shown that after a given period of time an arrangement of this kind no longer performs its appointed function.

It is also known as described in German Auslegeschrift No. 1,267,377 to fit, in the widened proximal part of the sleeve, a ball valve whose ball is pressed against a valve seating by a tangentially loaded helical spring but is able to move aside when the trocar or an instrument is passed through. This known design results in the sleeve having an eccentrically projecting widened portion and is expensive.

It is an object of the invention to simplify the construction of a ball valve and its fitting to a trocar sleeve of the kind described, with the valve seating accurately aligned, and to reduce manufacturing costs while providing a long life.

SUMMARY OF THE INVENTION

Accordingly, the invention consists in a trocar sleeve of the kind described, wherein the widened art forming the housing receives an insert of U-shaped cross-section and which may be made from a plastics material screwable to the plug to stress an inserted sealing gasket of deformation-resistant material which also may be a plastics material and which is to be drilled through to form a valve seating the space in the U formed by the insert forms a space for the ball of the ball valve to move in, which ball, before the insert is screwed to the plug, is connected to a shaft insertable in the insert and carrying a tangentially loaded helical spring placed under stress by connecting the insert to the plug.

By this means it is possible to stress the sealing gasket of deformation-resistant material and press it firmly into place while sealing off the internal passage when the U-shaped insert is screwed to the plug carrying the proximal portion of the sleeve and the gasket may then be apertured by a steeped drill inserted through the proximal portion of the sleeve, thus obtaining an absolutely central bore in the gasket and a satisfactory seating for the ball of the valve. A tangentially loaded helical spring which is free to move is freely inserted in the U-shaped insert and is held secure by the way in which it fits into the insert. The inert is then screwed up to the plug and the drilled out valve seating, the helical spring being placed under stress. The plug, together with the U-shaped insert, is then screwed into the widened part forming the housing.

The fitting of the spring mounting for the ball of the valve is particularly facilitated if, in a further embodiment, the ball of the ball valve is provided with a transverse groove opposite the valve seating to receive a flat tube receiving in turn a tangential portion of the helical spring bent into a hair-pin shape. The turns of the spring enclose the central section of an arch-shaped shaft inserted in recesses parallel to the axis of the insert located in the opposed sides of the U-shaped insert. The other tangential portion of the spring is supported in a notch in one of the sides of the U-shaped insert.

BRIEF DESCRIPTION OF THE DRAWINGS

In order that the invention may be more clearly understood, reference will now be made to the accompanying drawings which show one embodiment thereof by way of example and in which.

DETAILED DESCRIPTION OF PREFERRED EMBODIMENT

Figure 1:
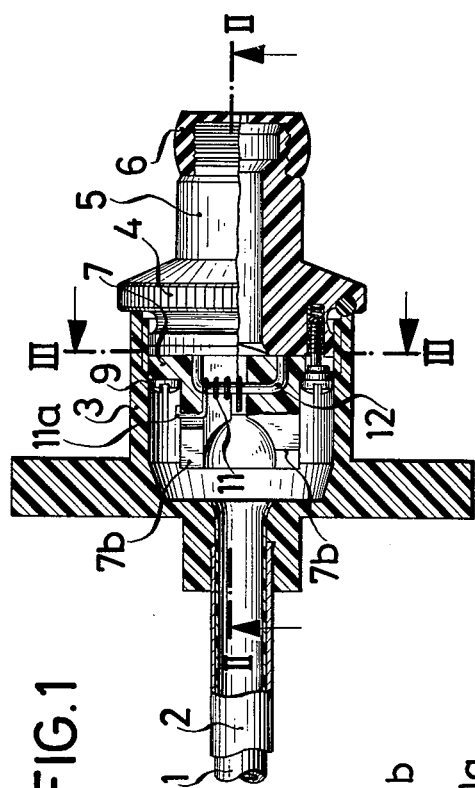
FIG. 1 is an axial section through the proximal part of a trocar sleeve with an interrupted side-view of the distal part thereof.

Referring now to the drawings, a metal trocar sleeve 2, (also referred to in the art as a trocar cannula) which is provided with an internal tubular insert 1 of insulating plastics material, is firmly connected at the proximal end to a widened part 3 forming a housing which can be closed off by a screw-in plug 4 carrying the proximal portion 5 of the sleeve. The housing part 3, the plug 4 and portion 5 of the sleeve likewise consist of a suitable plastics material in this embodiment. Portion 5 of the sleeve is provided with a rubber cap 6 having a central aperture to provide sealed passage for a trocar, a telescope, an endoscope or other instrument.

To seal off the trocar sleeve 1, 2 after the trocar or the instrument has been withdrawn, a ball valve is fitted in the widened housing part 2.

Figure 2:
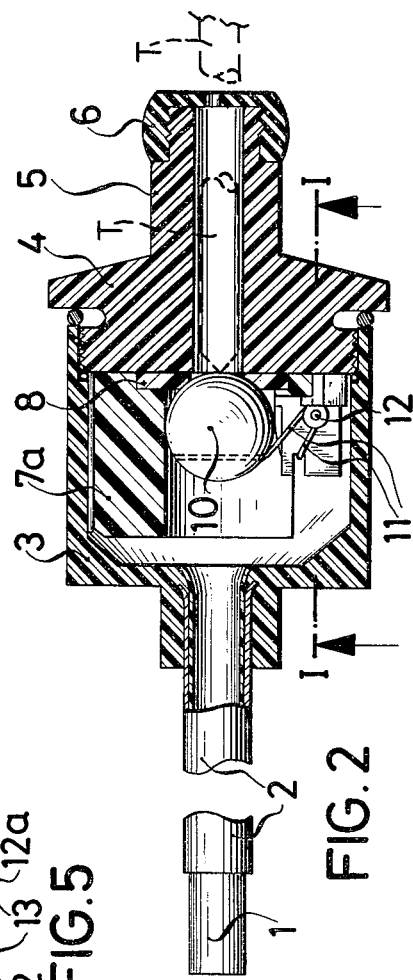
FIG. 2 is an axial section of the sleeve, viewed at right angles to FIG. 1.
Figure 3:
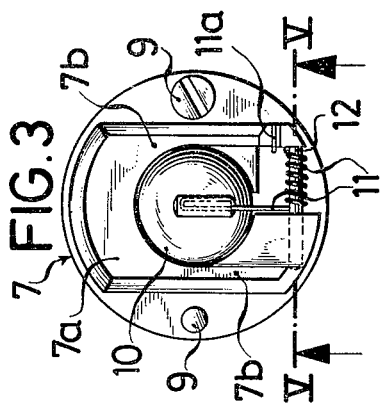
FIG. 3 is an end-on view of the insert looking from line III—III of FIG. 1.

In this embodiment this valve comprises an injection-moulded plastics insert 7 of U-shaped cross-section perpendicular to the axis of the sleeve as will be apparent from FIG. 3. On the plug side, the insert 7 is provided with a circular recess for the insertion of a sealing gasket 8 (FIG. 2) of heat-resistant and deformation-resistant material, such as a suitable plastics material, which can be pressed firmly into place under stress and while sealing off the internal passage, by connecting the insert 7 to the plug 4 by means of screws 9. After parts 7 and 4 have been screwed together, the sealing gasket 8 is provided with an exactly central bore of the requisite diameter by means of a stepped drill guided in portion 5 of the sleeve, and the resulting sealing ring then acts as a valve seating for the ball of a ball valve.

Figure 5:
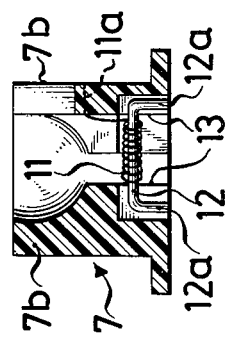
FIG. 5 is a section through the insert on line V—V of FIG. 2 or 3.
Figure 4:
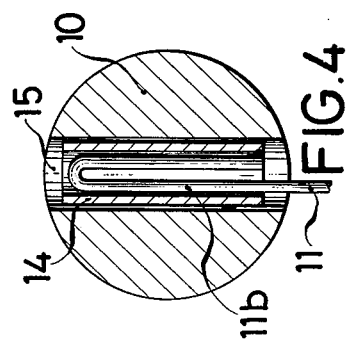
FIG. 4 is an enlarged scale end-on view of the side of the ball of the ball valve opposite the valve seating.

Before the valve-seating ring 8 is finally tightened down, or in other words before the insert 7 is finally connected to the plug 4, a unit consisting of a valve-ball 10 and a tangentially loaded helical spring 11 carried on an arch-shaped shaft 12 is inserted in the insert 7. For this purpose the sides 7b of the insert 7 are provided with recesses 13 parallel to the axis of the insert into which are fitted the side-sections 12a of the arch shaped shaft 12, onto whose central section the turns of the torsion spring 11 have been slid. One end 11a of the spring is hooked into a notch in one sidepiece 7b of the U (FIGS. 1, 3 and 5) and the other end 11b of the spring, which is bent into a hair-pin shape, is inserted in a flat tube 14 which is secured in a transverse groove 15 in the valve-ball 10 on the side remote from the plug 4 (FIG. 4). The free end of the hair-pin portion 11b is solidly connected to the tube 14, by welding for example.

In this way the valve-ball 10, together with its spring mounting 11 and the shaft 12 for the spring, is connected to the insert 7 while being free to move and is held fast in the insert 7, the spring being relaxed initially. Then, after the valve seating ring 8 has been inserted, the insert 7, together with the spring and the valve-ball, is screwed to the plug and at the same time the helical spring 11 is thus placed under stress, by which means the valve ball 10 is brought to bear against the valve seating 8.

The plug 4, together with the complete valve insert 7, is then screwed to the widened housing part 3 and fitting is thus complete.

To perforate the wall of a patient's abdomen, a trocar T is pushed through the cap 6 and trocar sleeve portion 5 and moves the valve ball off the seating by forcing it aside, the sealing function then being taken over by the rubber cap 6, the ball 10 being allowed a limited amount of movement on the hair-pin shaped tangential portion 11b of the spring 11, any damage to the valve-ball 10, which in any case is only subject to point or line contact, being largely obviated by its withdrawing movement and any breakage of the spring at the ends of its tangential portions being virtually impossible.

We claim:

1. In a trocar sleeve of the kind having a widened part forming a housing between the distal portion of said sleeve and its proximal portion, which latter extends from a plug for said widened housing part, and a ball valve in said widened housing part which ball valve is closable by resilient means and which is openable by a trocar passing through an opening in said plug and said sleeve, the improvement which consists in that said widened part forming the housing receives an insert said insert extending around said ball valve in a generally U-shaped configuration and thus affording a ball-receiving space, said insert is secured to said plug with a peripheral portion of the insert in clamping engagement with an inserted sealing gasket of deformation-resistant plastics material which is apertured to form a valve seating between the plug and insert, and in that the space presented by said insert forms a space for the ball of and thereby allow passage in said trocar sleeve of a trocar therethrough said ball valve to swing into and out of, said ball being biased by a tangentially loaded spring to seat in the aperture of said gasket, said spring being placed under stress by being connected to said insert, and said insert being separably attached to said plug, whereby said spring acts to automatically seat said ball valve against said gasket when said trocar is removed from said trocar sleeve and thereby prevent backflow of fluids through said trocar sleeve.

2. A trocar sleeve according to claim 1, wherein the ball of the ball valve is provided with a transverse groove opposite said valve seating with a tube secured to said groove and receiving a medially extended end portion of said spring, said spring having helical turns enclosing the central section of a shaft, which shaft is arch-shaped with its ends inserted in recesses parallel to the axis of said insert in the sides of said U-shaped insert adjacent said plug, the other end portion of said spring being supported in a recess in one of the side-pieces of said U-shaped insert.